(12) United States Patent
Sprinkle et al.

(10) Patent No.: US 7,290,546 B2
(45) Date of Patent: Nov. 6, 2007

(54) NASAL MASK

(75) Inventors: Tom Sprinkle, Rocky River, OH (US);
Mary B. Whitesel, Grafton, OH (US);
Mark E. Rosenkranz, Parma, OH (US)

(73) Assignee: Invacare Corporation, Elyria, OH (US)

( * ) Notice: Subject to any disclaimer, the term of this patent is extended or adjusted under 35 U.S.C. 154(b) by 516 days.

(21) Appl. No.: 10/394,731

(22) Filed: Mar. 22, 2003

(65) Prior Publication Data

US 2005/0011521 A1 Jan. 20, 2005

Related U.S. Application Data

(60) Provisional application No. 60/366,934, filed on Mar. 22, 2002.

(51) Int. Cl.
*A62B 18/08* (2006.01)
*A62B 18/02* (2006.01)
(52) U.S. Cl. .............................. 128/206.24; 128/207.13
(58) Field of Classification Search ........... 128/205.25, 128/206.11, 206.12, 206.13, 206.15, 206.18, 128/206.21, 206.24, 206.26, 206.27, 206.28, 128/207.11, 207.12, 207.13, 202.27; 24/307, 24/572.1, 573.09
See application file for complete search history.

(56) References Cited

U.S. PATENT DOCUMENTS

| | | |
|---|---|---|
| 781,516 A | 1/1905 | Guthrie, Jr. |
| 812,706 A | 2/1906 | Warbasse |
| 844,097 A | 2/1907 | Caldwell |
| 1,048,491 A | 12/1912 | Bulcher |
| 1,081,745 A | 12/1913 | Johnston et al. |
| 1,192,186 A | 7/1916 | Greene |
| 1,206,045 A | 11/1916 | Smith |
| 1,632,449 A | 6/1927 | McKesson |
| 1,635,275 A | 7/1927 | Johnson |
| 1,653,572 A | 12/1927 | Jackson |
| 1,926,027 A | 9/1933 | Biggs |
| 2,123,353 A | 7/1938 | Catt |
| 2,241,535 A | 5/1941 | Boothby et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |

(Continued)

FOREIGN PATENT DOCUMENTS

AU A-32914/95 2/1996

(Continued)

OTHER PUBLICATIONS

PCT Search Report from PCT/US2003/008773; pp. 1-9.

(Continued)

*Primary Examiner*—Teena Mitchell
(74) *Attorney, Agent, or Firm*—Calfee, Halter & Griswold, LLP

(57) ABSTRACT

A nasal mask assembly for preferred use in CPAP treatment. The mask assembly comprises a central body, a face cushion, a forehead support and a gas inlet. The gas inlet is rotatably connected to the central body, and the forehead support is pivotally connected to the central body. A method of using such a mask is also provided.

17 Claims, 13 Drawing Sheets

U.S. PATENT DOCUMENTS

| | | |
|---|---|---|
| 2,438,058 A | 3/1948 | Kincheloe |
| 2,578,621 A | 12/1951 | Yant |
| 2,765,788 A | 10/1956 | Raiche |
| 2,939,458 A | 6/1960 | Lundquist |
| 3,013,556 A | 12/1961 | Galleher, Jr. |
| 3,182,659 A | 5/1965 | Blout |
| 3,189,027 A | 6/1965 | Bartlett, Jr. |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins ................. 73/40 |
| 3,700,000 A | 10/1972 | Hesse et al. ............. 137/494 |
| 3,720,235 A | 3/1973 | Schrock ................. 138/137 |
| 3,725,953 A | 4/1973 | Johnson et al. ............ 2/14 W |
| 3,779,164 A | 12/1973 | Study ................... 101/334 |
| 3,982,532 A | 9/1976 | Halldin et al. ............ 128/146 |
| 4,077,404 A | 3/1978 | Elam .................. 128/145.8 |
| 4,167,185 A | 9/1979 | Lewis ................. 128/146.7 |
| 4,226,234 A | 10/1980 | Gunderson ........... 128/205.24 |
| 4,245,632 A | 1/1981 | Houston ............. 128/205.13 |
| 4,263,908 A | 4/1981 | Mizerak .............. 128/205.25 |
| 4,266,540 A | 5/1981 | Panzik et al. ......... 128/207.13 |
| 4,304,229 A | 12/1981 | Curtin ............... 128/201.11 |
| 4,328,797 A | 5/1982 | Rollins, III et al. ..... 128/202.27 |
| 4,347,205 A | 8/1982 | Stewart ................. 264/130 |
| 4,354,488 A | 10/1982 | Bartos ................ 128/205.25 |
| 4,402,316 A | 9/1983 | Gadberry ............. 128/201.15 |
| 4,412,537 A | 11/1983 | Tiger ................. 128/204.17 |
| 4,467,799 A | 8/1984 | Steinberg ............. 128/206.14 |
| 4,522,639 A | 6/1985 | Ansite et al. ............. 55/314 |
| 4,558,710 A | 12/1985 | Eichler ................. 128/720 |
| 4,559,940 A | 12/1985 | McGinnis ............ 128/206.26 |
| 4,616,647 A | 10/1986 | McCreadie ........... 128/206.19 |
| 4,622,964 A | 11/1986 | Flynn ................ 128/205.24 |
| 4,655,213 A | 4/1987 | Rapoport et al. ....... 128/205.25 |
| 4,665,570 A | 5/1987 | Davis ..................... 2/428 |
| 4,671,271 A | 6/1987 | Bishop et al. ......... 128/206.11 |
| 4,677,975 A | 7/1987 | Edgar et al. .......... 128/200.14 |
| 4,677,977 A | 7/1987 | Wilcox ............... 128/206.24 |
| 4,739,755 A | 4/1988 | White et al. .......... 128/206.12 |
| 4,770,169 A | 9/1988 | Schmoegner et al. .. 128/207.13 |
| 4,774,941 A | 10/1988 | Cook ................. 128/205.13 |
| 4,782,832 A | 11/1988 | Trimble et al. ........ 128/207.18 |
| 4,799,477 A | 1/1989 | Lewis ................ 128/206.24 |
| 4,809,692 A | 3/1989 | Nowacki et al. ....... 128/206.24 |
| 4,819,629 A | 4/1989 | Jonson ............... 128/203.22 |
| 4,821,713 A | 4/1989 | Bauman .............. 128/205.13 |
| 4,841,953 A | 6/1989 | Dodrill ............... 128/202.27 |
| 4,848,334 A | 7/1989 | Bellm ................ 128/207.11 |
| 4,848,366 A | 7/1989 | Aita et al. ............... 128/863 |
| 4,907,584 A | 3/1990 | McGinnis ............ 128/206.24 |
| 4,910,806 A | 3/1990 | Baker et al. ................ 2/452 |
| 4,919,128 A | 4/1990 | Kopala et al. ......... 128/207.18 |
| 4,938,210 A | 7/1990 | Shene ................ 128/203.12 |
| 4,938,212 A | 7/1990 | Snook et al. .......... 128/205.24 |
| 4,944,310 A | 7/1990 | Sullivan ................ 128/848 |
| 4,971,051 A | 11/1990 | Toffolon ............. 128/206.26 |
| 4,986,269 A | 1/1991 | Hakkinen ............ 128/204.23 |
| 4,989,596 A | 2/1991 | Macris et al. ......... 128/201.28 |
| 4,989,599 A | 2/1991 | Carter ................ 128/207.18 |
| 5,005,568 A | 4/1991 | Loescher et al. ....... 128/202.28 |
| 5,005,571 A | 4/1991 | Dietz ................. 128/205.25 |
| 5,038,776 A | 8/1991 | Harrison et al. ....... 128/207.11 |
| 5,042,473 A | 8/1991 | Lewis ................ 128/205.24 |
| 5,046,200 A | 9/1991 | Feder ..................... 2/452 |
| 5,063,922 A | 11/1991 | Hakkinen ............ 128/200.16 |
| 5,069,205 A | 12/1991 | Urso ................. 128/201.24 |
| 5,109,839 A | 5/1992 | Blasdell et al. ........ 128/203.12 |
| 5,109,840 A | 5/1992 | Daleiden ............. 128/205.13 |
| 5,117,819 A | 6/1992 | Servidio et al. ....... 128/204.18 |
| 5,121,745 A | 6/1992 | Israel ................ 128/202.28 |
| 5,133,347 A | 7/1992 | Huennebeck .......... 128/205.24 |
| 5,140,980 A | 8/1992 | Haughey et al. ....... 128/201.25 |
| 5,140,982 A | 8/1992 | Bauman .............. 128/205.13 |
| 5,159,938 A | 11/1992 | Laughlin ................ 128/858 |
| 5,178,138 A | 1/1993 | Walstrom et al. ...... 128/200.23 |
| 5,231,983 A | 8/1993 | Matson et al. ......... 128/207.14 |
| 5,233,978 A | 8/1993 | Callaway ............. 128/205.25 |
| 5,265,595 A | 11/1993 | Rudolph .............. 128/204.18 |
| 5,279,289 A | 1/1994 | Kirk .................. 128/205.23 |
| 5,280,784 A | 1/1994 | Kohler ............... 128/200.14 |
| 5,311,862 A | 5/1994 | Blasdell et al. ........ 128/205.25 |
| 5,322,057 A | 6/1994 | Raabe et al. .......... 128/203.12 |
| 5,343,878 A | 9/1994 | Scarberry et al. .......... 128/898 |
| 5,357,951 A | 10/1994 | Ratner ................ 128/205.24 |
| 5,372,130 A | 12/1994 | Stern et al. ........... 128/205.25 |
| 5,388,571 A | 2/1995 | Roberts et al. ........ 128/203.12 |
| 5,404,871 A | 4/1995 | Goodman et al. ...... 128/200.14 |
| 5,419,318 A | 5/1995 | Tayebi ............... 128/205.27 |
| 5,429,126 A | 7/1995 | Bracken .............. 128/207.11 |
| 5,429,683 A | 7/1995 | Le Mitoard .......... 128/206.24 |
| 5,431,158 A | 7/1995 | Tirotta ............... 128/206.21 |
| 5,438,981 A | 8/1995 | Starr et al. ........... 128/205.24 |
| 5,441,046 A | 8/1995 | Starr et al. ........... 128/207.11 |
| 5,477,852 A | 12/1995 | Landis et al. ......... 128/207.18 |
| 5,479,920 A | 1/1996 | Piper et al. ........... 128/204.23 |
| 5,488,948 A | 2/1996 | Dubruille et al. ....... 128/207.11 |
| 5,492,116 A | 2/1996 | Scarberry et al. ....... 128/206.24 |
| 5,501,214 A | 3/1996 | Sabo ................. 128/205.24 |
| 5,509,404 A | 4/1996 | Lloyd et al. ........... 128/200.14 |
| 5,517,986 A | 5/1996 | Starr et al. ........... 128/206.24 |
| 5,538,000 A | 7/1996 | Rudolph .............. 128/205.25 |
| 5,540,223 A | 7/1996 | Starr et al. ........... 128/205.25 |
| 5,546,936 A | 8/1996 | Virag et al. ........... 128/207.14 |
| 5,558,090 A | 9/1996 | James ................ 128/207.18 |
| RE35,339 E | 10/1996 | Rapoport ............. 128/204.18 |
| 5,560,354 A | 10/1996 | Berthon-Jones et al. ................. 128/205.25 |
| 5,570,682 A | 11/1996 | Johnson .............. 128/200.14 |
| 5,570,689 A | 11/1996 | Starr et al. ........... 128/207.11 |
| 5,592,938 A | 1/1997 | Scarberry et al. ....... 128/206.24 |
| 5,608,647 A | 3/1997 | Rubsamen et al. ........ 364/509 |
| 5,642,730 A | 7/1997 | Baran ................ 128/207.14 |
| 5,647,355 A | 7/1997 | Starr et al. ........... 128/205.24 |
| 5,647,357 A | 7/1997 | Barnett et al. ........ 128/206.24 |
| 5,649,532 A | 7/1997 | Griffiths ............. 128/206.24 |
| 5,649,533 A | 7/1997 | Oren ................. 128/207.12 |
| 5,655,520 A | 8/1997 | Howe et al. .......... 128/203.13 |
| 5,655,527 A | 8/1997 | Scarberry et al. ....... 128/206.24 |
| 5,657,752 A | 8/1997 | Landis et al. ......... 128/207.13 |
| 5,662,101 A | 9/1997 | Ogden et al. ......... 128/205.25 |
| 5,666,946 A | 9/1997 | Langenback .......... 128/200.16 |
| 5,673,690 A | 10/1997 | Tayebi et al. ......... 128/206.24 |
| D385,960 S | 11/1997 | Rudolph .............. D24/110.4 |
| 5,685,296 A | 11/1997 | Zdrojkowski et al. .. 128/205.24 |
| 5,690,102 A | 11/1997 | Bertheau et al. ....... 128/207.11 |
| D388,873 S | 1/1998 | Richards et al. ........ D24/110.4 |
| 5,715,814 A | 2/1998 | Ebers ................ 128/206.18 |
| 5,724,965 A | 3/1998 | Handke et al. ........ 128/207.13 |
| 5,738,094 A | 4/1998 | Hoftman ............. 128/206.26 |
| 5,746,201 A | 5/1998 | Kidd ................. 128/206.24 |
| 5,758,642 A | 6/1998 | Choi ................. 128/206.21 |
| 5,813,423 A | 9/1998 | Kirchgeorg .......... 128/202.28 |
| 5,832,918 A | 11/1998 | Pantino .............. 128/205.25 |
| D402,755 S | 12/1998 | Kwok ................ D24/110.4 |
| 5,884,624 A | 3/1999 | Barnett et al. ........ 128/206.24 |
| 5,887,587 A | 3/1999 | Groenke ............. 128/207.13 |
| 5,896,857 A | 4/1999 | Hely et al. ........... 128/205.24 |
| 5,921,239 A | 7/1999 | McCall et al. ........ 128/205.25 |

| | | | | | | |
|---|---|---|---|---|---|---|
| D412,745 S | 8/1999 | Scheu | D24/110.4 | EP | 0054154 | 10/1981 |
| 5,937,851 A | 8/1999 | Serowski et al. | 128/202.27 | EP | 0178925 | 10/1985 |
| 5,937,855 A | 8/1999 | Zdrojkowski et al. | 128/205.24 | EP | 0252052 | 7/1987 |
| 5,941,245 A | 8/1999 | Hannah et al. | 128/207.11 | EP | 0264772 A1 | 10/1987 |
| 5,954,052 A | 9/1999 | McDonald et al. | 128/206.27 | EP | 0386605 A1 | 2/1990 |
| D428,987 S | 8/2000 | Kwok | D24/110.4 | EP | 0427474 A2 | 11/1990 |
| D428,988 S | 8/2000 | Smart | D24/110.4 | EP | 0462701 A1 | 5/1991 |
| 6,112,746 A | 9/2000 | Kwok et al. | 128/207.13 | EP | 0602424 B1 | 11/1993 |
| D435,650 S | 12/2000 | Kwok | D24/110.4 | EP | 0608684 A1 | 1/1994 |
| 6,341,383 B1 * | 1/2002 | Beltrani | 2/452 | EP | 0697225 B1 | 7/1995 |
| 6,357,441 B1 | 3/2002 | Kwok et al. | 128/207.13 | EP | 0747078 | 6/1996 |
| 6,374,826 B1 * | 4/2002 | Gunaratnam et al. | 128/206.27 | EP | 0821978 A2 | 7/1997 |
| 6,467,483 B1 | 10/2002 | Kopacko et al. | | EP | 1 027 905 A2 | 8/2000 |
| 6,520,182 B1 * | 2/2003 | Gunaratnam | 128/206.27 | EP | 1 266 674 A | 12/2002 |
| 6,532,961 B1 * | 3/2003 | Kwok et al. | 128/206.21 | FR | 1 100 270 | 5/1954 |
| 6,550,070 B2 * | 4/2003 | Wiegand | 2/421 | FR | 2574657 A1 | 6/1986 |
| 6,679,261 B2 * | 1/2004 | Lithgow et al. | 128/207.11 | FR | 2658725 A1 | 8/1991 |
| 6,691,707 B1 * | 2/2004 | Gunaratnam et al. | 128/206.21 | FR | 2749176 A1 | 12/1997 |
| 6,694,532 B2 * | 2/2004 | Chen | 2/428 | GB | 848215 | 9/1960 |
| 6,832,610 B2 * | 12/2004 | Gradon et al. | 128/206.27 | GB | 1395391 | 5/1975 |
| 2001/0035188 A1 | 11/2001 | Gleason et al. | 128/205.25 | GB | 1467828 | 3/1977 |
| 2002/0005198 A1 | 1/2002 | Kwok et al. | 128/205.25 | GB | 2145335 A | 3/1985 |
| 2002/0005201 A1 | 1/2002 | Gradon et al. | 128/207.11 | GB | 2164569 | 3/1986 |
| 2002/0014241 A1 | 2/2002 | Gradon et al. | 128/205.25 | GB | 2147506 A | 4/1987 |
| 2002/0023649 A1 | 2/2002 | Gunaratnam et al. | 128/205.25 | GB | 2267648 A | 7/1996 |
| 2002/0023650 A1 | 2/2002 | Gunaratnam et al. | 128/205.25 | JP | 9216240 A | 8/1997 |
| 2002/0026934 A1 | 3/2002 | Lithgow et al. | 128/97.1 | WO | WO 80/01044 | 5/1980 |
| 2002/0029780 A1 | 3/2002 | Frater et al. | 128/206.24 | WO | WO 82/03548 | 10/1982 |
| 2002/0029781 A1 | 3/2002 | Kwok et al. | 128/207.13 | WO | WO 86/06969 | 12/1986 |
| 2002/0083948 A1 | 7/2002 | Kwok et al. | 128/206.24 | WO | WO 87/01950 | 4/1987 |
| 2002/0104540 A1 | 8/2002 | Kwok et al. | 128/205.25 | WO | WO 91/03277 | 3/1991 |
| 2002/0108613 A1 | 8/2002 | Gunaratnam et al. | 128/205.25 | WO | WO 92/15353 | 9/1992 |
| 2002/0134388 A1 | 9/2002 | Chang | | WO | WO 92/20395 | 11/1992 |
| 2002/0148473 A1 | 10/2002 | Kwok et al. | 128/207.11 | WO | WO 93/01854 | 2/1993 |
| 2002/0157672 A1 | 10/2002 | Gunaratnam et al. | 128/205.25 | WO | WO 94/16759 | 8/1994 |
| 2002/0185134 A1 | 12/2002 | Bishop | | WO | WO 94/20051 | 9/1994 |
| 2003/0019495 A1 | 1/2003 | Palkon et al. | 128/206.21 | WO | WO 95/02428 | 1/1995 |
| 2003/0075180 A1 | 4/2003 | Raje et al. | | WO | WO 96/17643 | 6/1996 |
| | | | | WO | WO 96/25983 | 8/1996 |

FOREIGN PATENT DOCUMENTS

| | | |
|---|---|---|
| AU | A-41018/97 | 4/1998 |
| AU | A-89312/98 | 1/1999 |
| AU | 712236 | 11/1999 |
| AU | 724360 | 9/2000 |
| AU | 728849 | 1/2001 |
| CA | 1039144 | 9/1978 |
| CA | 2261790 | 2/1998 |
| CA | 2295457 | 7/2000 |
| CA | 2298129 | 8/2000 |
| DE | 159396 A | 3/1905 |
| DE | 207751 | 4/1907 |
| DE | 459104 C1 | 4/1928 |
| DE | 701690 C1 | 1/1941 |
| DE | 1104122 | 4/1961 |
| DE | 3015279 A1 | 10/1981 |
| DE | 3345067 A1 | 5/1985 |
| DE | 3537505 A1 | 4/1987 |
| DE | 3539073 A1 | 5/1987 |
| DE | 4004157 C1 | 4/1991 |
| DE | 4343205 A1 | 6/1995 |
| DE | 19735359 A1 | 1/1998 |
| DE | 29723101 U1 | 5/1998 |
| DE | 3707952 A1 | 9/1998 |
| DE | 29810846 U1 | 12/1999 |
| DE | 199 62 515 A 1 | 7/2001 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |
| WO | WO 00/57942 | 10/2000 |
| WO | WO 00/78381 | 12/2000 |
| WO | WO 00/78381 A1 | 12/2000 |
| WO | WO 00/78382 A1 | 12/2000 |
| WO | WO 00/78383 A1 | 12/2000 |
| WO | WO 00/78384 | 12/2000 |
| WO | WO 00/78384 A1 | 12/2000 |
| WO | WO 02/45784 A1 | 6/2002 |
| WO | WO 03/082406 A | 10/2003 |

OTHER PUBLICATIONS

PCT Search Report and Written Opinion from PCT/US2004/016192; pp. 1-22.

Communication pursuant to Article 96(2) EPC for European application No. 03 745 562.3-2310.

* cited by examiner

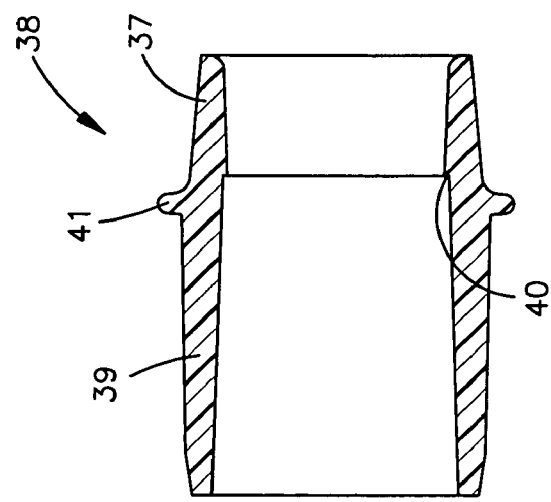
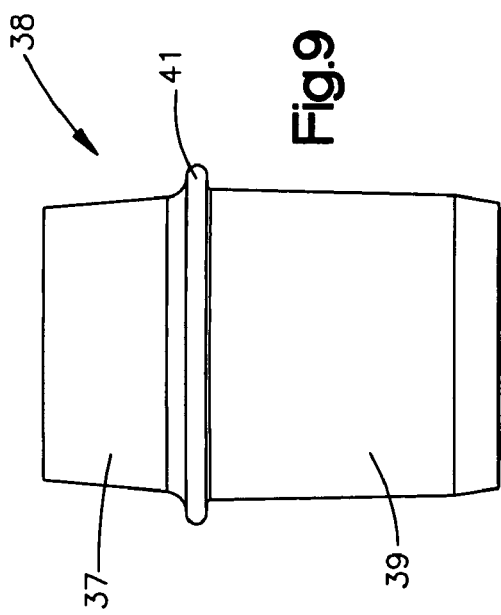
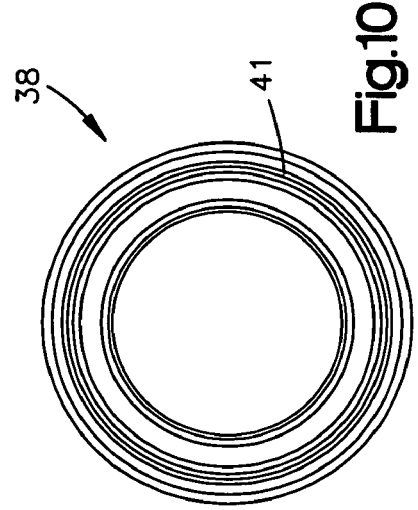

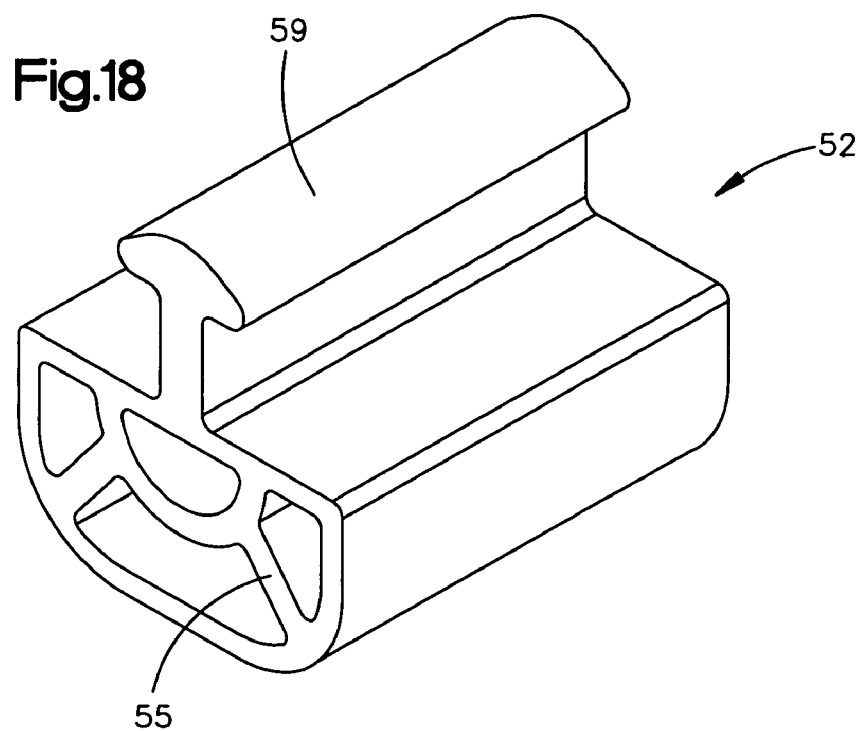
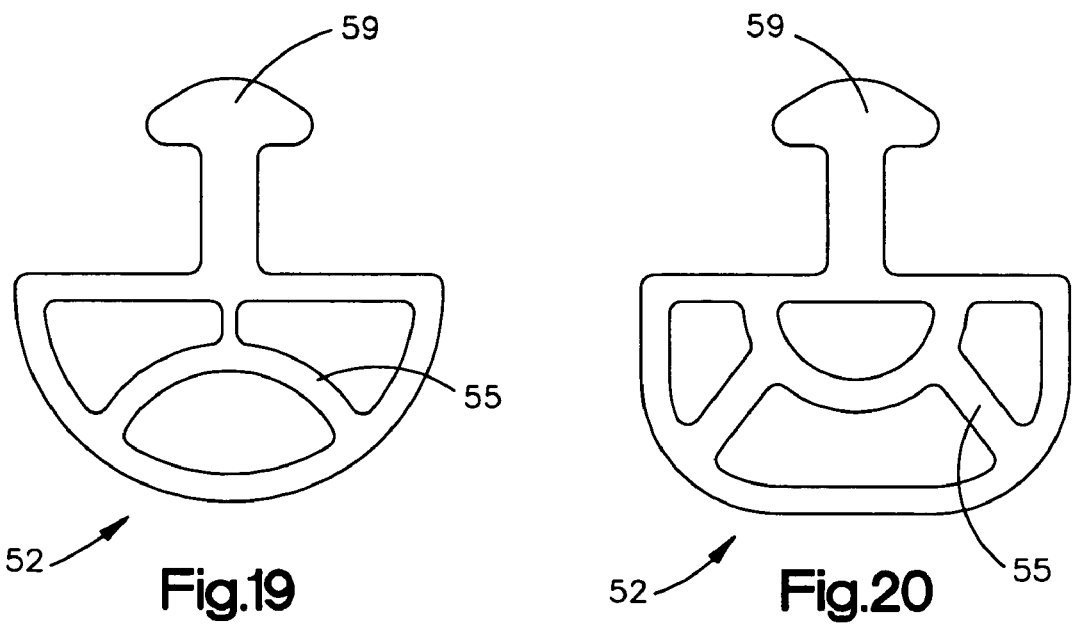

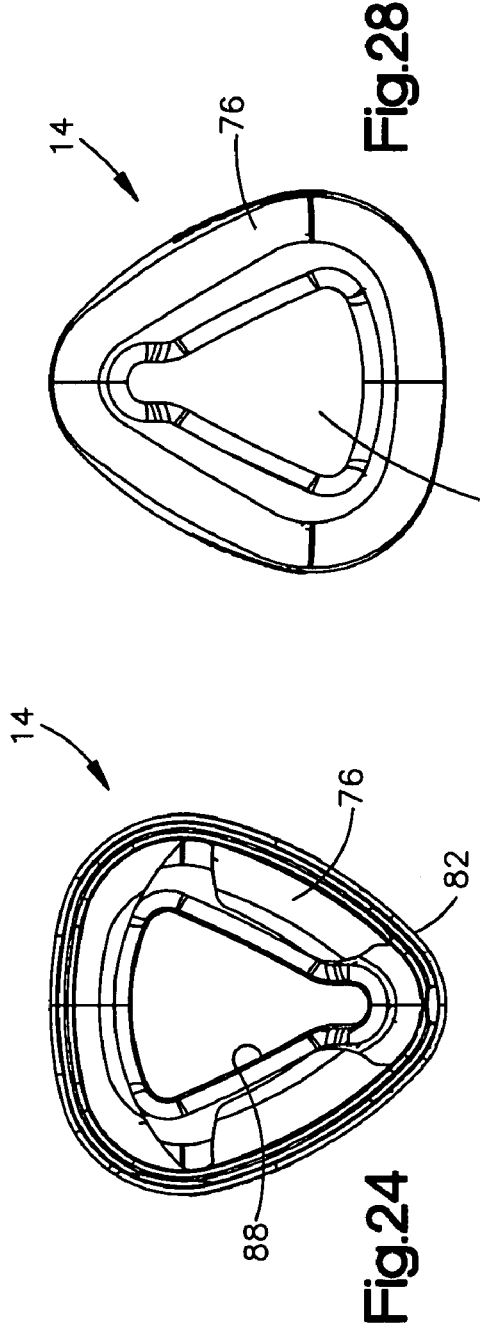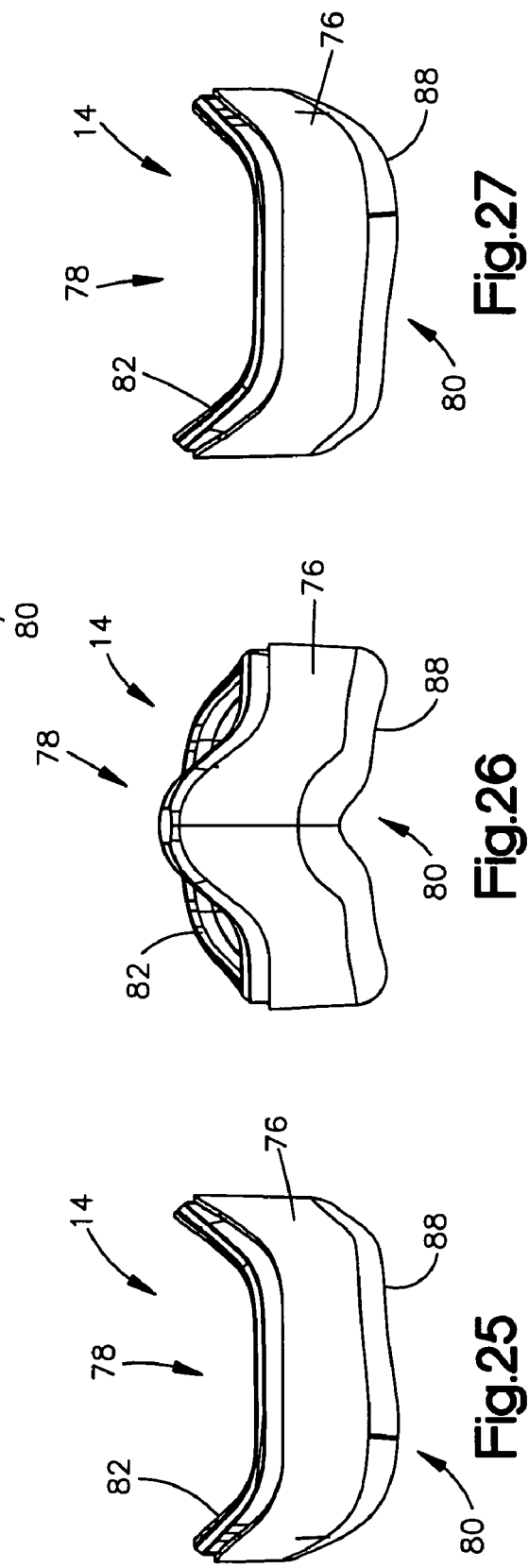

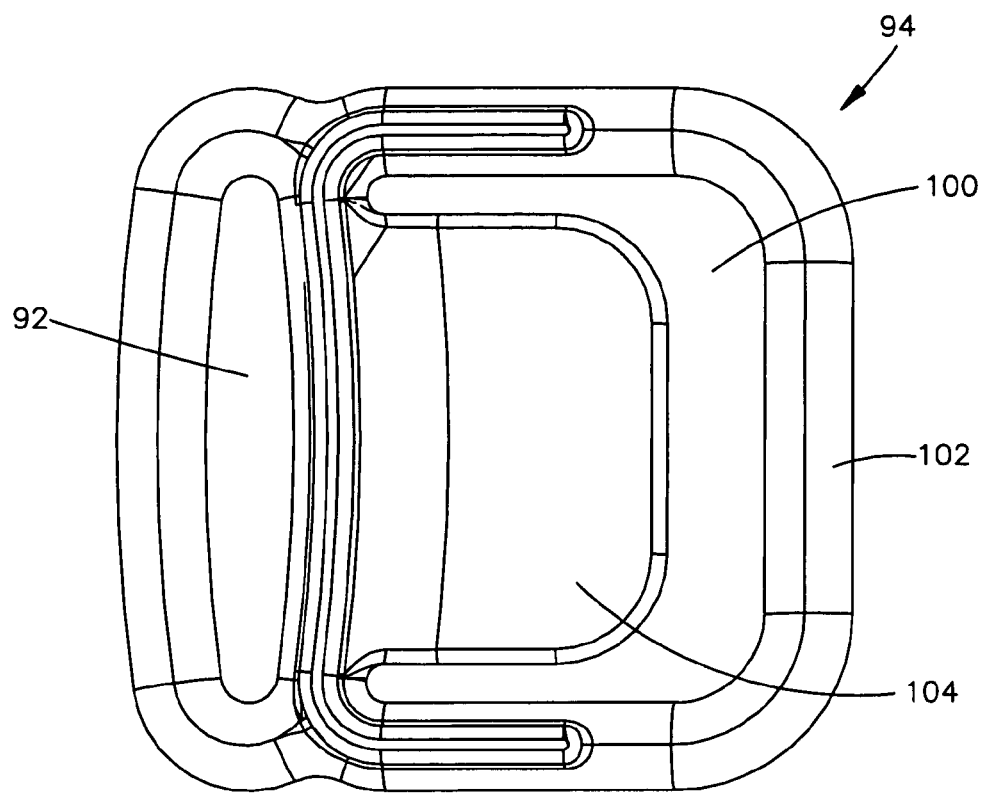
Fig.32
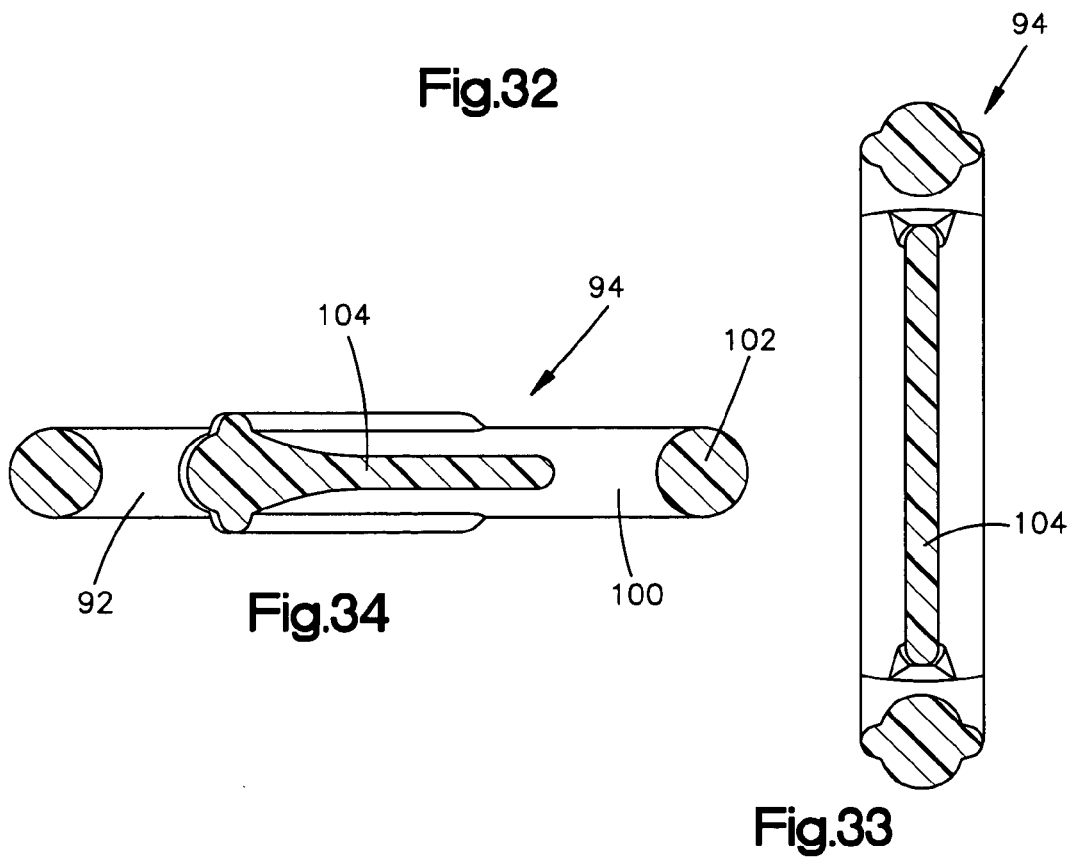
Fig.34
Fig.33

NASAL MASK

RELATED APPLICATIONS

This application claims the benefit of U.S. Provisional patent application Ser. No. 60/366,934 filed on Mar. 22, 2002, the entire disclosure of which is fully incorporated herein by reference.

BACKGROUND AND SUMMARY OF THE INVENTION

This invention pertains to a nasal mask. Nasal masks may be used to deliver gases of controlled composition, at a controlled pressure, and at a controlled flow to a person's nasal passages for inhalation. Gas composition typically is controlled to achieve a particular medical goal, such as anesthesiology. Gas pressure typically is controlled to ease or assist the breathing process, made difficult for example due to high altitude or a medical condition afflicting the user.

The nasal mask described here is particularly useful with continuous positive airway pressure ("CPAP") treatment for sleep disorders, such as obstructive sleep apnea. Pursuant to this treatment the user wears a nasal mask while sleeping. As will be readily understood by one of ordinary skill in the art, a device delivers air to the nasal mask at a pressure above atmospheric pressure. This helps the user to breathe more normally during sleep. Further descriptions of CPAP treatments and devices can be found in U.S. Pat. Nos. 5,199,424 and 5,433,193, which are hereby fully incorporated by reference. The mask may be used in the home as well as institutional settings such as long term care facilities.

The nasal mask described here also is particularly useful in a bi-level or non-invasive ventilator. As a preferred embodiment it may be used to treat chronic obstructive pulmonary disease (COPD), congested heart failure (CHF), and/or gastro esophageal reflux disorder (GERD).

The nasal mask described here has a lower profile than prior art masks. This has several advantages. It allows less restricted head movement by the user, permits quicker and less expensive manufacturing, and provides a better aesthetic appearance. One or more of these advantages may encourage treatment compliance by persons who may benefit from treatment requiring use of nasal masks.

The nasal mask described here further has an improved forehead cushion support. The position of the forehead cushion support is variable, so that a single mask may fit different persons with differently sloping foreheads. This variability permits a single mask design to fit several different persons, thus obviating to some extent the need for making masks of differing sizes. The forehead cushions also are removable from their support to allow more easy and better cleaning, as well as easy replacement. They are nonetheless attached securely to prevent them falling off unintentionally.

DESCRIPTION OF THE FIGURES

FIG. 9 shows a side view of a rotation fitting for use in a nasal mask assembly.

FIG. 10 shows a top view of a rotation fitting for use in a nasal mask assembly.

FIG. 11 shows a cross-sectional view of a rotation fitting for use in a nasal mask assembly, taken along line A-A in FIG. 10.

FIG. 18 shows a perspective view of a forehead cushion for use in a nasal mask assembly.

FIG. 19 shows a side view of a forehead cushion for use in a nasal mask assembly.

FIG. 20 shows a side view of a forehead cushion for use in a nasal mask assembly.

FIG. 24 shows a front view of a face cushion for use in a nasal mask assembly.

FIG. 25 shows a side view of a face cushion for use in a nasal mask assembly.

FIG. 26 shows a top view of a face cushion for use in a nasal mask assembly.

FIG. 27 shows a side view of a face cushion for use in a nasal mask assembly.

FIG. 28 shows a rear view of a face cushion for use in a nasal mask assembly.

FIG. 32 shows a plan view of a strap attachment for use in a nasal mask assembly.

FIG. 33 shows a sectional view of the strap attachment of FIG. 32, taken along line C-C of FIG. 32.

FIG. 34 shows another sectional view of the strap attachment of FIG. 32, taken along line B-B of FIG. 32.

WRITTEN DESCRIPTION OF PREFERRED EMBODIMENTS

Figure 1:
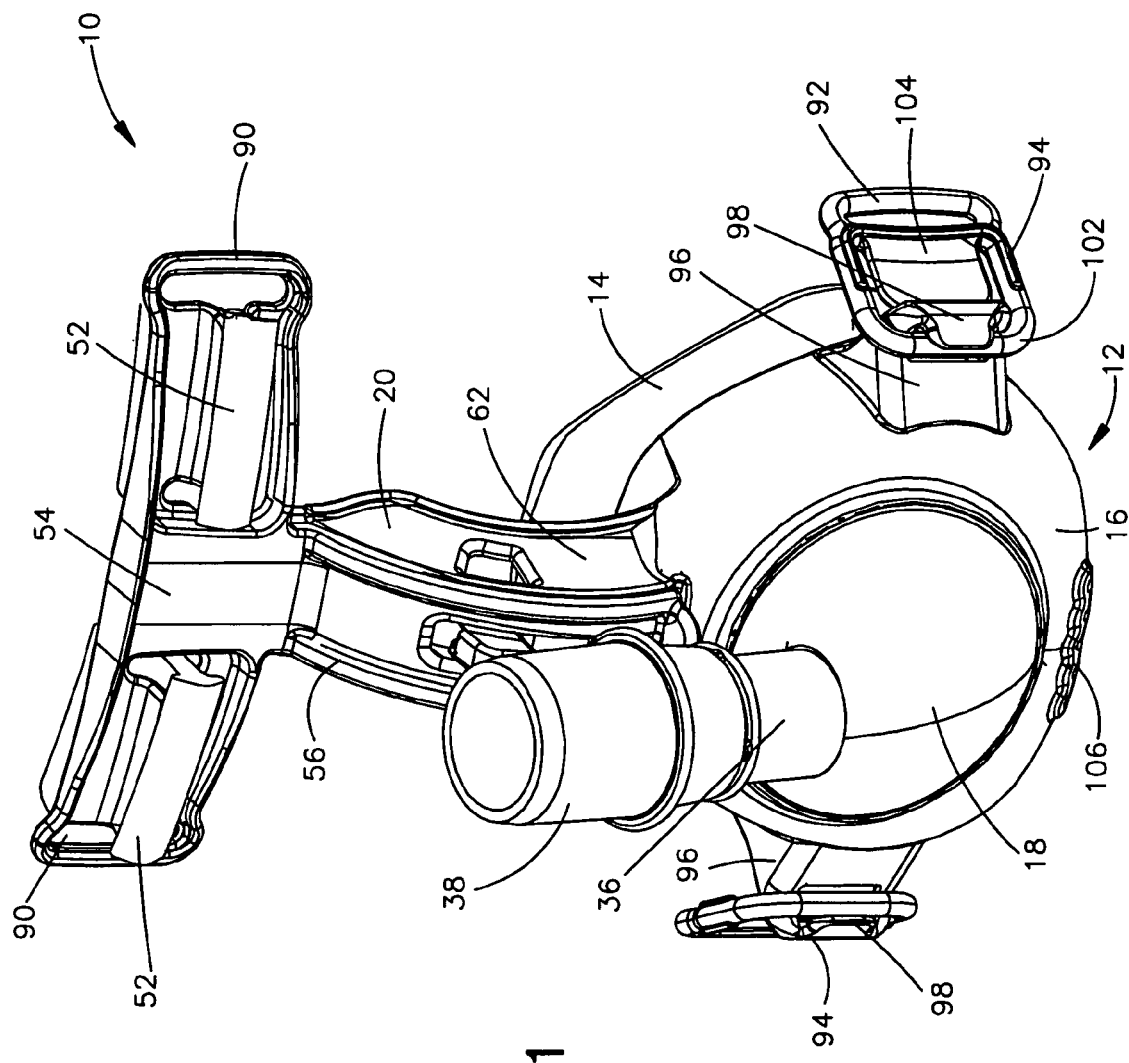
FIG. 1 shows a perspective view of a nasal mask assembly.
Figure 2:
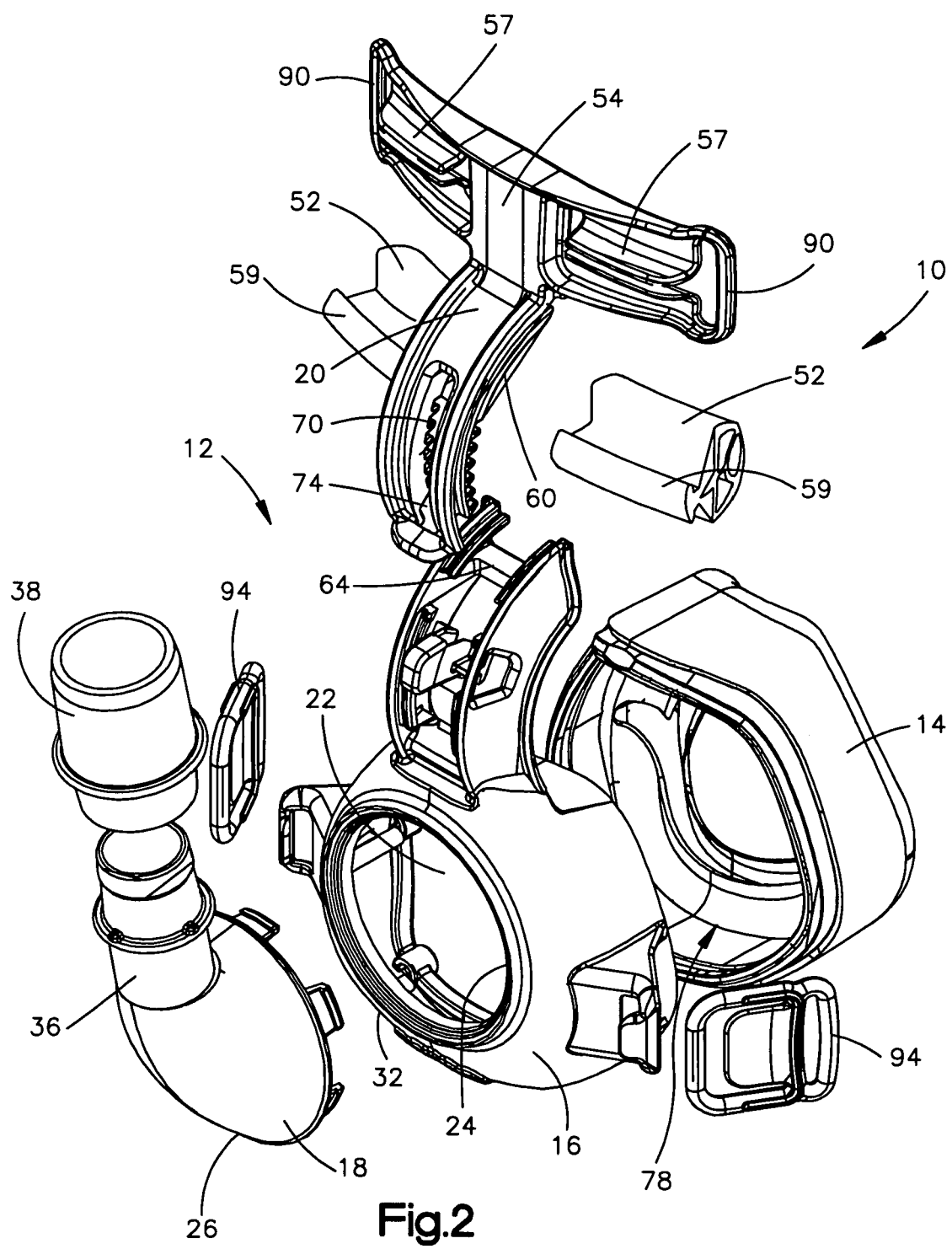
FIG. 2 shows a front perspective view of the nasal mask assembly shown in FIG. 1 with the component parts disassembled.
Figure 3:
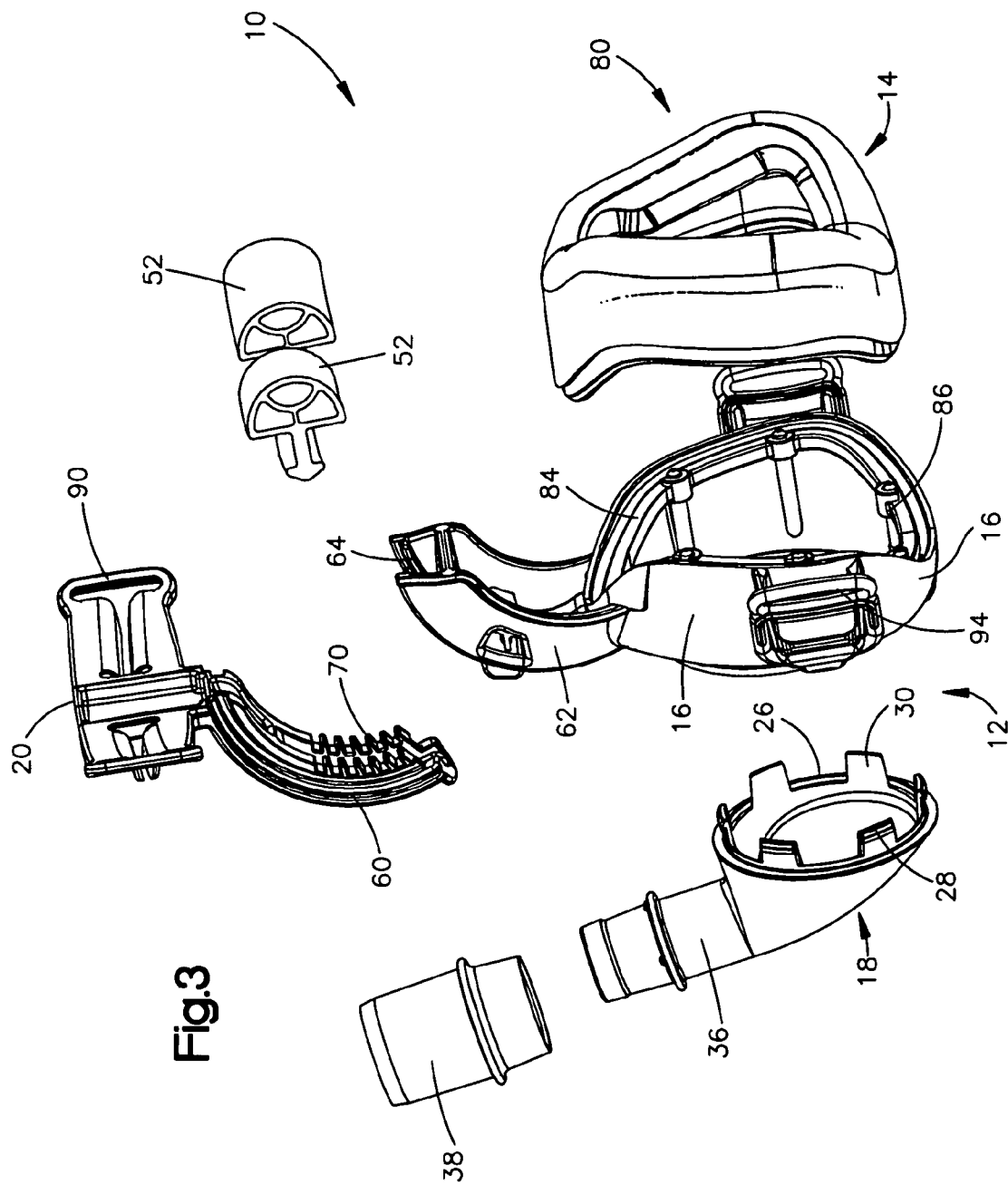
FIG. 3 shows a rear perspective view of the nasal mask assembly shown in FIG. 1 with the component parts disassembled.
Figure 4:
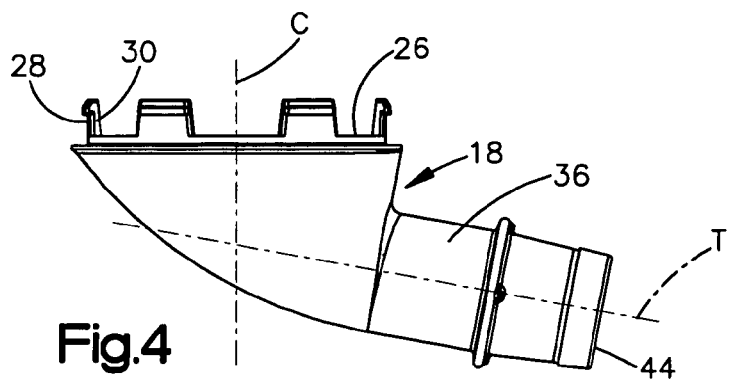
FIG. 4 shows a side view of a gas inlet for use in a nasal mask assembly.
Figure 5:
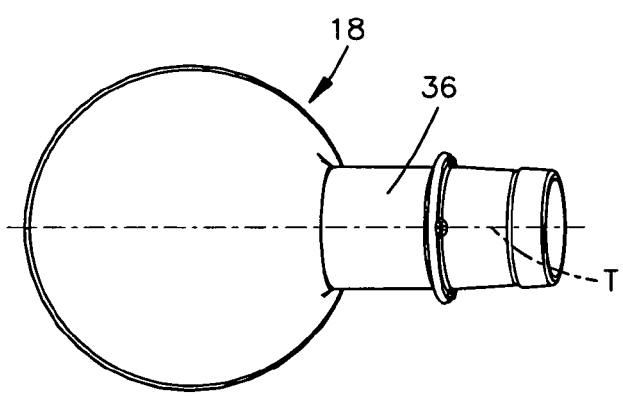
FIG. 5 shows a front view of a gas inlet for use in a nasal mask assembly.
Figure 7:
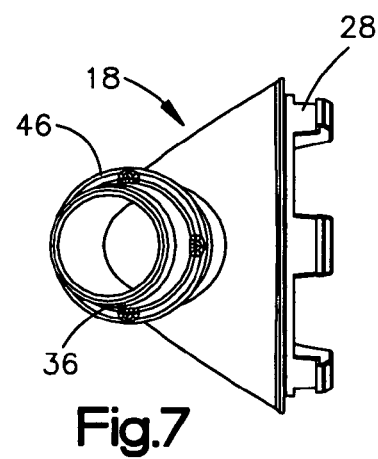
FIG. 7 shows a bottom view of a gas inlet for use in a nasal mask assembly.
Figure 6:
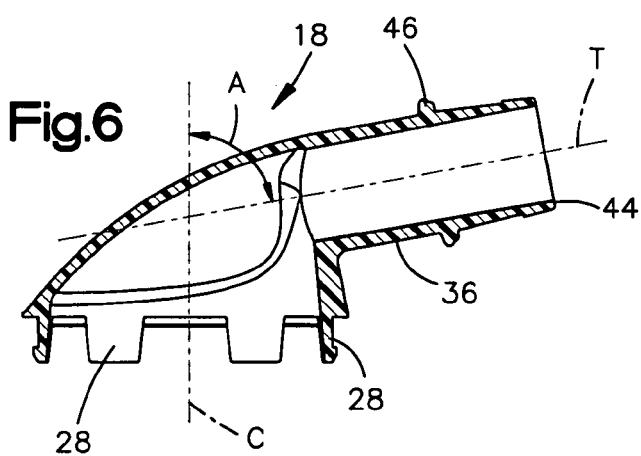
FIG. 6 shows a cross-sectional front view of a gas inlet for use in a nasal mask assembly, taken along line A-A of FIG. 5.
Figure 8:
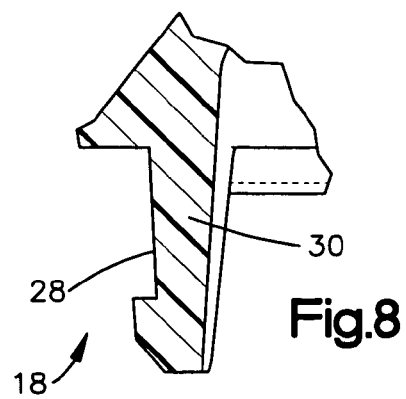
FIG. 8 shows a detail of FIG. 6, as indicated by line E in FIG. 6.
Figure 14:
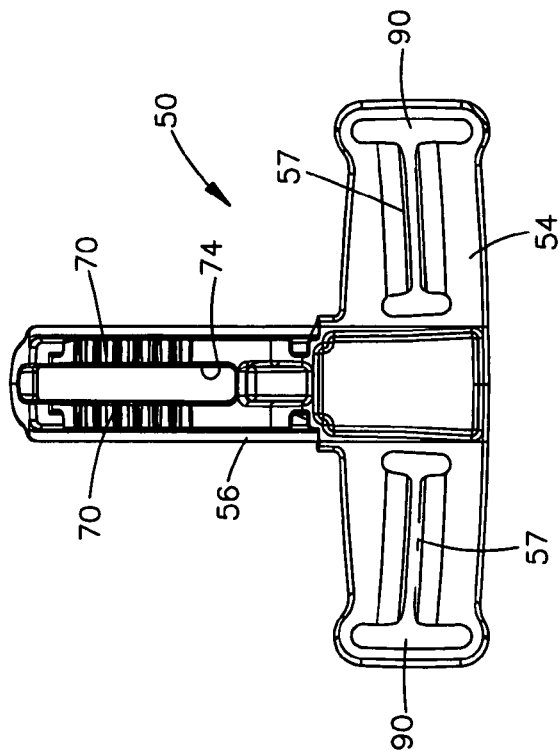
FIG. 14 shows a rear view of a forehead frame for use in a nasal mask assembly.
Figure 12:
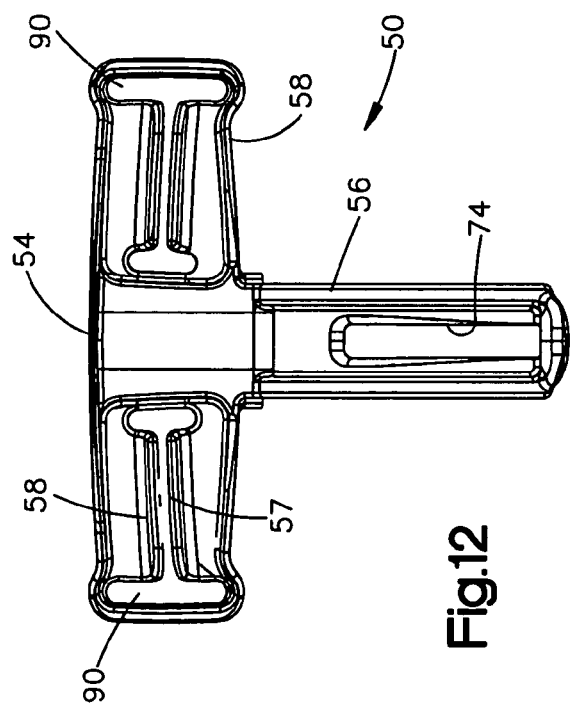
FIG. 12 shows a front view of a forehead frame for use in a nasal mask assembly.
Figure 13:
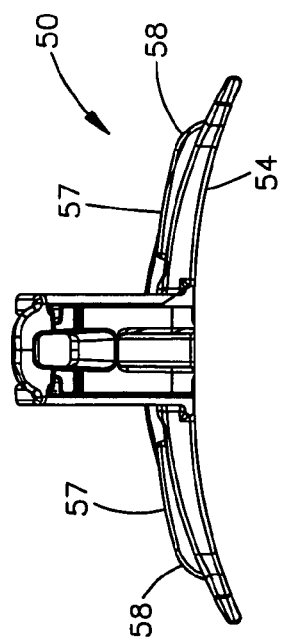
FIG. 13 shows a bottom view of a forehead frame for use in a nasal mask assembly.
Figure 17:
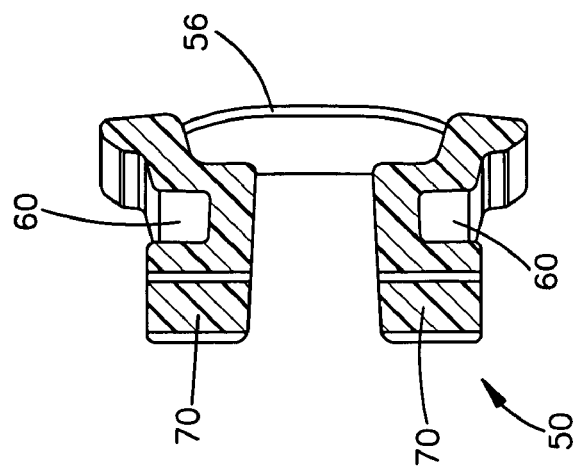
FIG. 17 shows a cross-sectional view of a forehead frame for use in a nasal mask assembly, taken along line D-D of FIG. 15.
Figure 16:
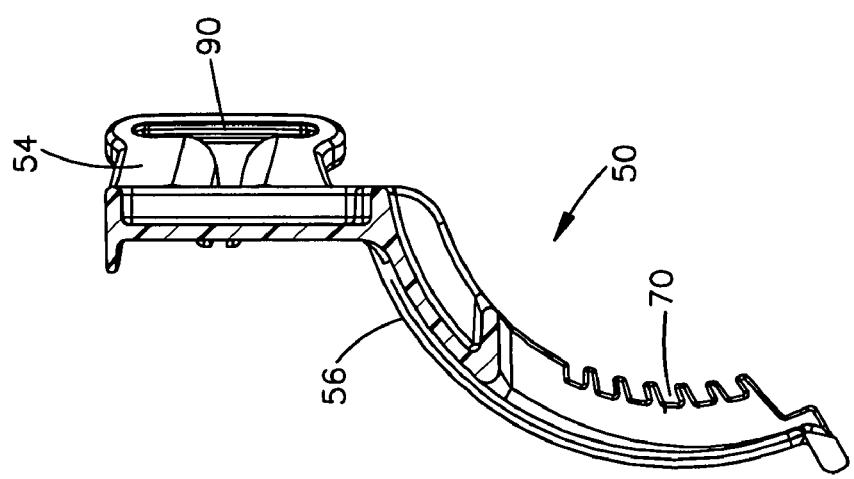
FIG. 16 shows a cross-sectional view of a forehead frame for use in a nasal mask assembly, taken along line A-A of FIG. 12.
Figure 15:
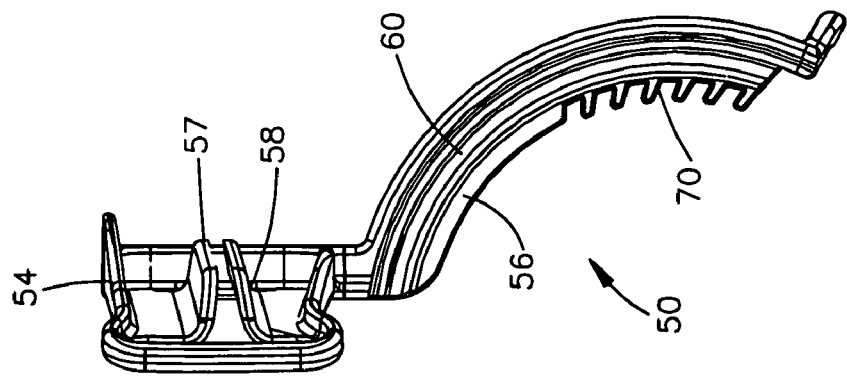
FIG. 15 shows a side view of a forehead frame for use in a nasal mask assembly.

A preferred nasal mask assembly 10 is shown in the accompanying drawings, with FIGS. 1-3 showing the entire assembly as a whole and the remaining Figures detailing the particular parts. The nasal mask 10 has two main components, a shell 12 and a face cushion 14. The shell component 12 is preferably made of plastic, which is preferably optically transparent. The plastic should be impermeable to gas or air. The shell component 12 has several parts, including a central body 16, a gas inlet 18 and a forehead support 20.

The central body 16 defines a central cavity 22. A circular inlet aperture 24 in the front of the central body 16 permits air to enter the central cavity 22. The gas inlet 18 is rotatably attached to the central body 16 so that it covers the circular aperture 24. One of ordinary skill in the art will know several methods of rotatably attaching the gas inlet 18 over the circular aperture 24.

In the embodiment shown in FIGS. 4-8, for example, the gas inlet 18 defines a circular edge portion 26 having several flanges 30, each with a groove 28. The flanges 30 along the circular edge portion 26 extend into the central cavity 22 of the central body 16. The central body rim 32, which defines the circular aperture 24, snaps in behind the grooves 28 of the flanges 30, thereby sealing against the release of air from within the cavity 22 or gas inlet 18 to the outside environment.

The gas inlet 18 extends to a cylindrical tube portion 36 having a tube axis T, oriented with respect to the center axis C of the gas inlet 18 at a tube angle A. Where the tube portion 36 extends parallel to the circular aperture's center axis C the tube angle A is zero (0) degrees. Where the tube portion 36 extends perpendicular to the circular aperture's center axis C the tube angle A is ninety (90) degrees. The tube angle A of the nasal mask 10 may be anywhere from between about 0 and about 130 degrees. The upper limit for the tube angle A is dictated solely by the need to avoid the tube (not shown in drawings) interrupting head movement as much as possible. The tube angle A is preferably between 0 and about 90 degrees, more preferably between about 60 and about 90 degrees, and most preferably between about 75 and about 90 degrees. That preferred range permits the tube portion 36 to be made with a relatively lower profile than is available in the prior art.

The cylindrical tube portion 36 connects to a flexible gas delivery tube (not shown in the drawings) in such a way that the tube may rotate with respect to the cylindrical tube portion 36. One of ordinary skill in the art will know of various suitable rotatable connections. For example, FIGS. 9-11 show a rotation fitting 38 for connecting the tube to the tube portion 36. The rotation fitting 38 has two cylindrical portions, one having a smaller diameter 37 than the other 39, thereby defining an interior shelf 40 within the rotation fitting 38. The cylindrical tube portion 36 may exhibit a fitting ring 44 at its end for snap fitting within the interior shelf 40 of the rotation fitting 38. Or, the cylindrical tube portion 36 may alternatively exhibit several flanged projections 42 (not shown in the drawings), similar to the flanges 30 of the gas inlet 18, for providing a snap fit with the rotation fitting 38. The cylindrical tube portion 36 may further have an external ring 46. The smaller diameter portion 37 of the rotation fitting 38 slides on to the tube portion 36 of the mask 10 until it abuts the external ring 46. At that point either the fitting ring 44 just barely projects into the larger diameter 39 portion of the rotation fitting 38, and snaps out on to the interior shelf 40. The fitting ring 44 therefore keep the rotation fitting 38 from sliding off of the tube portion 36, but also permits rotational movement between the elements. The tube then slides on to the larger diameter portion 39 of the rotation fitting 38, preferably stopped by a tube ring 41, and is held there by frictional forces.

The nasal mask 10 includes a forehead support 20 comprising a forehead frame 50 and forehead cushions 52. The forehead frame 50, as shown for example in FIGS. 12-17, has a horizontal member 54, on which the forehead cushions 52 are mounted, and a vertical member 56. The forehead cushions 52, shown in FIGS. 18-20, are mounted on the horizontal member 54 in a removable manner. One example of a removable mount is shown in the drawings as raised walls 57 in the horizontal member 54 slidably receiving grooved ends 59 of a cushion 52. A cushion 52 may be removed from the horizontal member 54 by sliding it toward a vertical slot 90 at the end of the horizontal member 54. A ramp 58 adjacent the slot 90 permits easy removal of the forehead cushion 52 without allowing the forehead cushion 52 to unintentionally be removed. One of ordinary skill will know of other ways to attach a forehead cushion 52 to a supporting frame 50 in a removable manner.

The forehead cushions 52 are preferably made of a bio-friendly material such as silicone. The cushion may have internal ribs 55 of various configurations (two are shown in the drawings) to impart sufficiently flexible support. While two cushions 52 are shown in the drawings, any number of cushions 52 may be used in practice, for example 1, 3, 4 or more. Or no cushions may be used.

Figure 23:
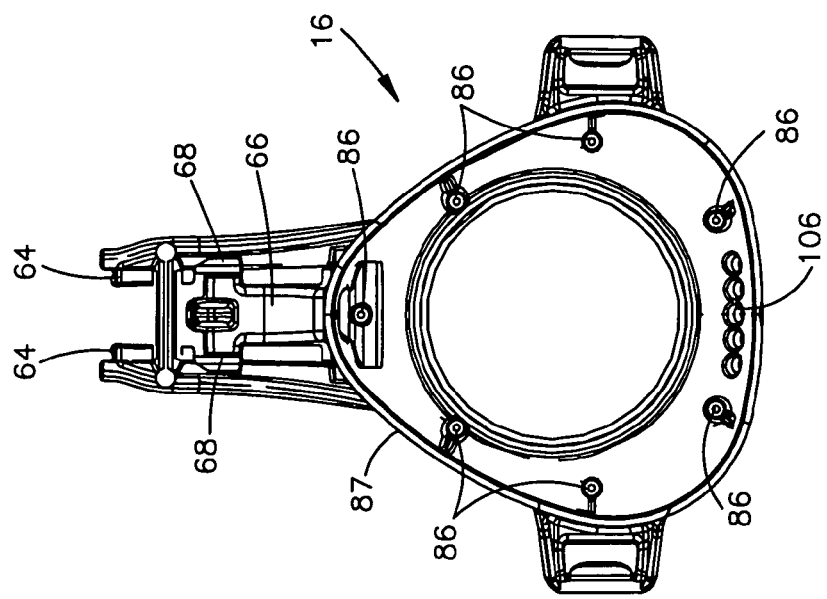
FIG. 23 shows a rear view of a central body for use in a nasal mask assembly.
Figure 22:
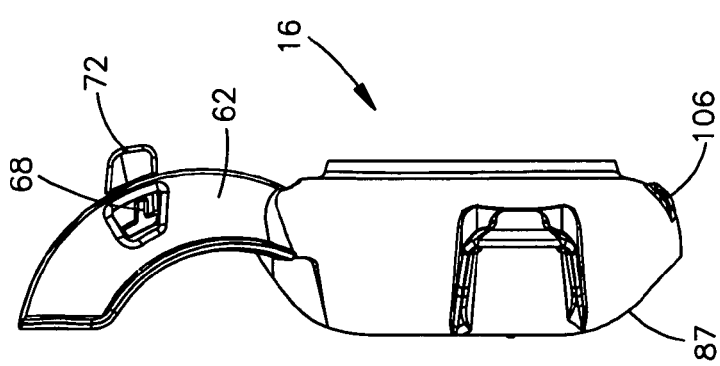
FIG. 22 shows a side view of a central body for use in a nasal mask assembly.
Figure 21:
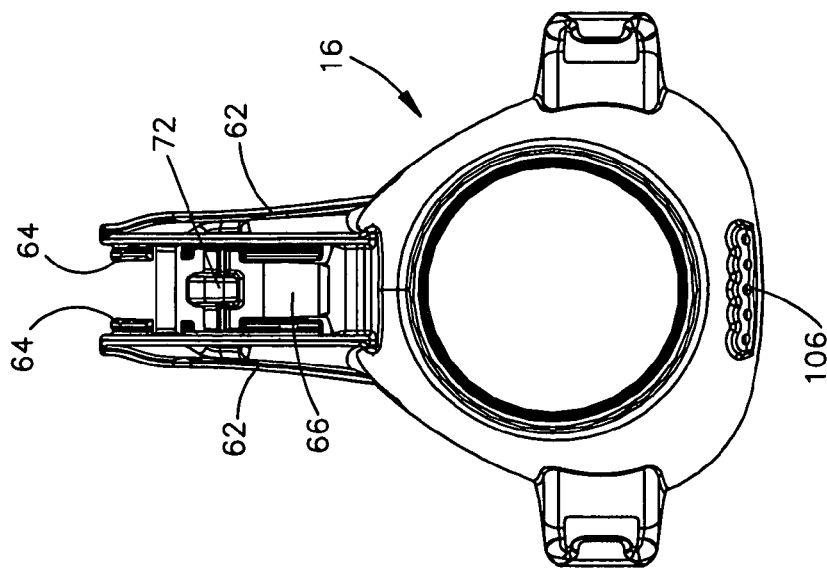
FIG. 21 shows a front view of a central body for use in a nasal mask assembly.
Figure 29:
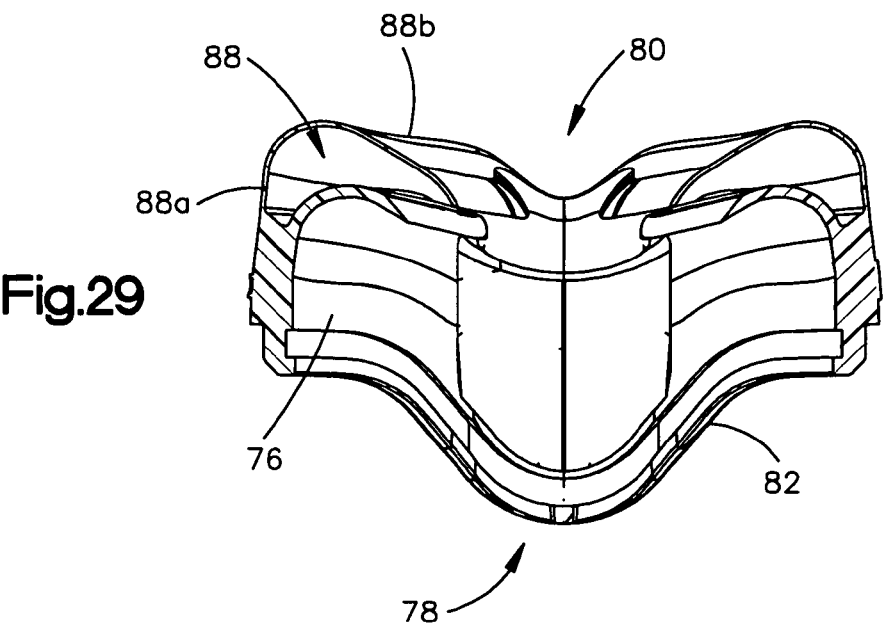
FIG. 29 shows a cross-sectional view of a face cushion for use in a nasal mask assembly, taken along line B-B of FIG. 27.
Figure 30:
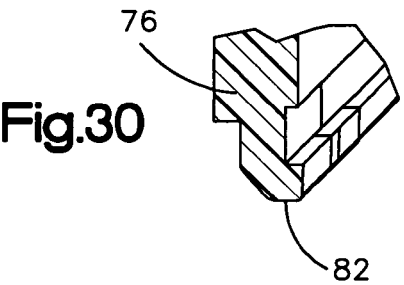
FIG. 30 shows a detail of FIG. 31, as indicated by line H in FIG. 31.
Figure 31:
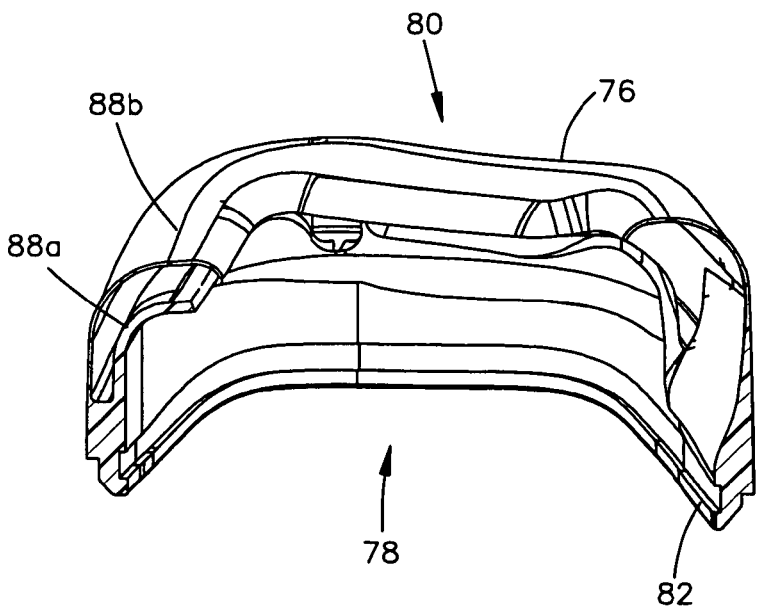
FIG. 31 shows a cross-sectional view of a face cushion for use in a nasal mask assembly, taken along line A-A of FIG. 26.
Figure 36:
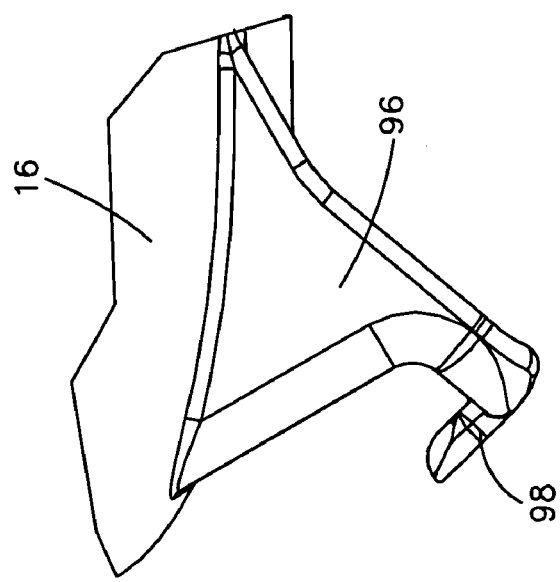
FIGS. 35 and 36 show views of a strap arm for use in a nasal mask assembly.
Figure 35:
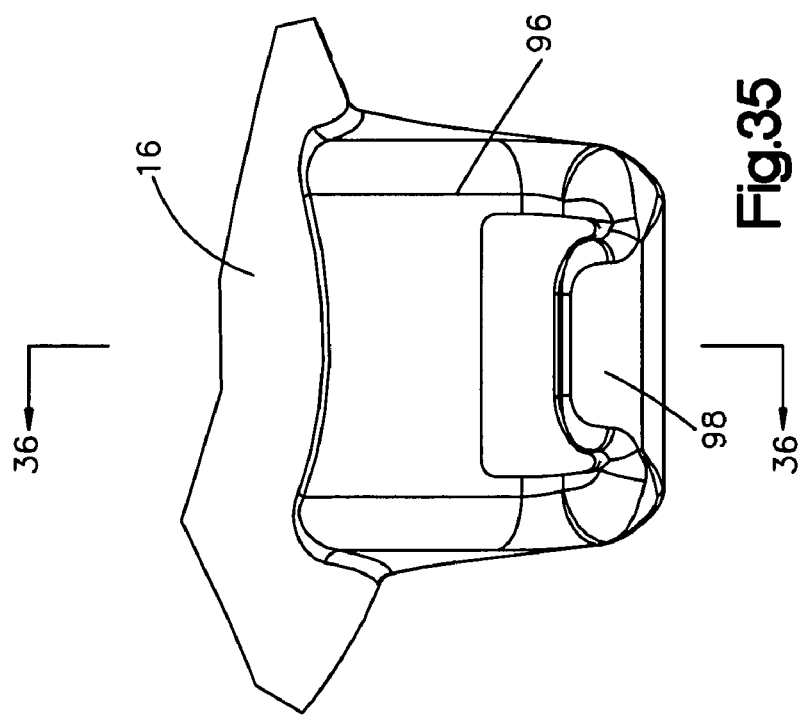

The vertical member 56 of the forehead frame 50 attaches to the central body 16 of the nasal mask 10. The vertical member 56 has two arcuate grooves 60, one in each side. Two arms 62, preferably arcuate in shape, extend from the top of the central body 16 as shown in FIGS. 21-23. Each arm 62 has an inwardly extending ridge 64 for mating with a groove 60 in the vertical member 56 of the forehead support 20. This arcuate ridge-in-groove attachment permits the forehead frame 50 to pivot with respect to the central body 16, thereby accommodating user foreheads of differing slope.

The nasal mask 10 may include structure for maintaining the forehead support 20 at one of two or more discrete positions relative to the central body 16. One of ordinary skill in the art will know of many ways to do this. For example, the drawings show a positioning arm 66 extending from the central body 16, between the two arms 62. The positioning arm 66 may alternatively, or in addition, extend from one or both arms 62. The positioning arm 66 has two projections 68, which each may mate with one or more dips 70 in the underside of the forehead frame vertical member 56. Each dip 70 represents a discrete position of the forehead frame 50 with respect to the central body 16. The positioning arm 66 is flexible to permit bending the arm 66 down so that the projections 68 exit a dip 70, and the forehead support 20 may be shifted to another position.

The nasal mask 10 may further include structure for stopping the forehead support 48 at two extreme positions with respect to the central body 16. There are several ways to do this, as will be known to one of ordinary skill in the art. In the embodiment shown in the drawings, a central tab 72 extends from the positioning arm 66 and into an aperture 74 in the vertical member 56 of the forehead frame 50. The forehead frame 50 reaches one of its two extreme positions when the tab 72 reaches the upper or lower end of the aperture 74.

A preferred face cushion component 14 for the mask 10 is shown in FIGS. 24-31. The face cushion 14 serves two basic functions: user comfort and sealing. Thus the face cushion 14 should be made of a bio-friendly elastomeric material which is both substantially gas impermeable and elastic enough to conform comfortably to the contours of a person's face. A preferred material is silicone. The face cushion 14 may take any shape; the shape shown in the drawings is preferred.

The face cushion 14 comprises a cushion body 76 having two opposed openings, a mask-side or "front" opening 78 and a face-side or "rear" opening 80. The front rim 82 defining the front opening 78 sealingly fits into the rear of the shell's central body 16 in any one of several ways which will be known to one of ordinary skill in the art. FIG. 3, for example, shows a brace 84 supported within the central body 16 by several posts 86 (six are shown in the Figures). The brace 84 is shaped to conform to the contour of the central body's 16 rear rim 87, leaving sufficient space between them such that the front rim 82 of the cushion 14 snugly (and substantially air-tightly) fits into the space. Thus the brace 84 acts to secure the cushion 14 to the central body 16.

The cushion body 76 extends from the front rim 82 to the rear rim 88. The cushion body 76 is sufficiently long that its elastomeric properties can provide a cushioning effect between the nasal mask 10 and the user's face when the mask 10 is worn, but not so long to make the mask 10 cumbersome to use during sleep. The cushion body 76 is sufficiently thick to provide cushioning and to prevent deformation due to pressure on the nasal mask 10 when tightened down on to the user's head.

The rear opening 80 of the face cushion 14 is defined by a double rim 88. An inner 88a and outer 88b rim extend inwardly from the cushion body 76. The outer rim 88b is relatively thin so that it may more easily conform to the contours of different persons' faces. Pressurized air entering the mask 10 from the tube sealingly presses the outer rim 88b against the user's face. The inner rim 88a is thicker than the outer rim 88b to provide better support for the mask 10 against the user's face, but preferably is thin enough to provide for some adjustment against the contours of the user's face.

For the most efficient operation, the nasal mask 10 should be held against the user's face. This ensures a sufficiently tight seal so that an elevated pressure is maintained within the mask 10 and the gas delivered to the mask 10 does not leak to the outside environment. The mask 10 may be held against the user's face by hand, but that is generally not satisfactory over long periods of time.

Therefore the nasal mask 10 may include strap slots 92 for attaching straps (not shown) to the mask 10. A strap end may be looped through a strap slot 92 and then secured, preferably with a snap or hook and loop connection. The strap then may be wrapped around the user's head and adjusted to provide a tight enough fit for maintaining a proper seal, but loose enough for the comfort of the user. The strap slots 92 are preferably located on opposite sides of the central body 16, and perhaps on opposite sides of the horizontal member 54 of the forehead support 20 (for example, slots 90 may be used as strap slots in addition to providing a sliding entry for the cushions 52). One of ordinary skill in the art will know of several alternatives.

The strap slots 92 may be formed integrally with a portion of the nasal mask shell 12, such as illustrated in the drawings of the slot 90. Alternatively the strap slots 92 may be part of a strap attachment 94, such as illustrated in FIG. 1 and FIGS. 32-36. The strap attachment 94 slips over a strap arm 96 on the central body 16. A holder 98 on the strap arm 96 projects up into an aperture 100 in the strap attachment 94. Thus the holder fits over and around a holder bar 102, as shown in FIG. 1. A flexible tab 104 prevents the holder 98 from exiting the aperture 100 unless and until the strap attachment 94 is rotated around the holder 98 far enough that the flexible tab 104 snaps off of the holder 98 by flexing around to the front of the holder 98. Use of the strap attachment 94 permits the strap to be easily attached to and detached from the central body 16, with a minimal risk that the strap will be accidentally detached as the user rolls around during sleep.

The nasal mask 10 disclosed herein may be used in the following manner. First the user puts the mask 10 on his or her head and adjusts the head straps to achieve a comfortable but sealingly tight fit. A machine operates to supply air of a desired composition and pressure to a tube, as known in the art. The supplied air travels through the tube and into the tube portion 36 of the mask 10. From there it travels into the mask shell's central cavity 22, through the face cushion's front and rear openings 78, 80 and into the user's nasal passageways, to be inhaled by the user.

The nasal mask 10 described herein may incorporate one or more exhaust ports 106 to permit gas exhaled by the user (e.g. carbon dioxide) to exit the mask 10 before the user's next inhalation. The exhaust port(s) 106 may be located somewhere in the face cushion 14, in the central body 16, in the gas inlet 18, or even in the tube somewhere proximate the nasal mask 10. In the drawings the exhaust ports 106 are shown in the central body 16. One of ordinary skill in the art will know of several exhaust port designs which permit exhaust of gas exhaled by the user, and also do not permit exhaust of gas supplied through the tube.

The presently disclosed mask 10 is a nasal mask only. This device may easily be modified to become a combined nasal/mouth mask by making the central cavity 16 and face cushion 14 large enough to encompass the user's nose and mouth. Or, use of two separate nasal and mouth bodies connected by an airway conduit may be preferable to maintain a better seal with the user's face or for some other reason. Other methods of making a combined nasal/mouth mask may be known to one of ordinary skill in the art. Similarly the presently disclosed device may be made as a mouth mask only.

While the present invention has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departing from the spirit or scope of the applicant's general inventive concept.

We claim:

1. A nasal mask comprising:
   a central body, the central body comprising an inlet aperture for receiving a delivered amount of gas, the central body having a rear rim;
   a gas inlet rotatably disposed around the inlet aperture of the central body, the gas inlet comprising a central axis and a tube portion, wherein the tube portion receives the delivered amount of gas and has a tube axis, and wherein a tube angle is formed between the tube axis and the central axis of the gas inlet and the tube angle is between about 0 degrees and about 130 degrees; and a face cushion attached to the central body and having a front rim; and a brace supported within the central body, being shaped to conform to the contour of the central body's rear rim, leaving sufficient space between the brace and the rear rim that the front rim of the face cushion fits snugly and substantially air-tightly into the space, the brace thus acting to secure the cushion to the central body.

2. The nasal mask of claim 1 wherein the tube angle is between about 0 degrees and about 90 degrees.

3. The nasal mask of claim 1 wherein the tube angle is between about 60 degrees and about 90 degrees.

4. The nasal mask of claim 3 wherein the forehead support is pivotably connected to the central body.

5. The nasal mask of claim 1 wherein the tube angle is between about 75 degrees and about 90 degrees.

6. The nasal mask of claim 1 further comprising a forehead support connected to the central body and a forehead cushion removably mounted to the forehead support.

7. The nasal mask of claim 1 further comprising a rotation fitting having a first end and a second end, wherein the first end is rotatably disposed around the tube portion, and the second end receives a tube which supplies gas.

8. The nasal mask of claim 1 further comprising a gas inlet rotatably disposed around the inlet aperture of the central body and a rotation fitting having a first end and a second end, wherein the first end is rotatably disposed around the tube portion, and the second end receives a tube which supplies gas.

9. A nasal mask as set forth in claim 1 wherein the central body comprises a strap arm, the strap arm comprising a holder;

the mask comprising a strap attachment comprising a holder bar and a flexible tab with a holder space disposed in between the holder bar and the flexible tab;

wherein, when the mask is worn by a user, the holder projects into the space between the holder bar and the flexible tab; and wherein the holder fits over and around the holder bar, the flexible tab preventing the holder from exiting the holder space unless and until the strap attachment is rotated around the holder far enough that the flexible tab snaps off the holder by flexing around the front of the holder.

10. A nasal mask comprising:

a central body, the central body comprising an inlet aperture for receiving a delivered amount of gas and a strap arm, the strap arm comprising a holder;

a strap attachment comprising a holder bar and a flexible tab with a space disposed in between the holder bar and the flexible tab;

wherein, when the mask is worn by a user, the holder projects into the space between the holder bar and the flexible tab, the flexible tab acting on the holder to maintain the holder in the space; and a face cushion attached to the central body.

11. The nasal mask of claim 10 further comprising a forehead support connected to the central body and a forehead cushion removably mounted to the forehead support.

12. The nasal mask of claim 11 wherein the forehead support is pivotably connected to the central body.

13. A nasal mask as set forth in claim 10 wherein the holder fits over and around the holder bar, the flexible tab preventing the holder from exiting the aperture unless and until the strap attachment is rotated around the holder far enough that the flexible tab snaps off the holder by flexing around the front of the holder.

14. A nasal mask as set forth in claim 13 wherein:

the mask comprises a brace supported within the central body, being shaped to conform to the contour of the central body's rear rim, leaving sufficient space between the brace and the rear rim that the front rim of the face cushion fits snugly and substantially air-tightly into the space, the brace thus acting to secure the cushion to the central body.

15. A nasal mask as set forth in claim 10 wherein:

the mask comprises a brace supported within the central body, being shaped to conform to the contour of the central body's rear rim, leaving sufficient space between the brace and the rear rim that the front rim of the face cushion fits snugly and substantially air-tightly into the space, the brace thus acting to secure the cushion to the central body.

16. A method of using a nasal mask and a strap, wherein the nasal mask comprises a strap arm having a holder and the strap comprises a first end attached to the mask and a second end attached to a strap attachment, the method comprising:

placing the nasal mask against a user's face;

connecting the second end of the strap to the nasal mask by placing a holder bar of the strap attachment over the holder of the nasal mask; and turning on a supply of pressurized gas connected to the nasal mask;

wherein the holder projects into a space between the holder bar and a flexible tab of the strap attachment, the flexible tab acting on the holder to maintain the holder in the space.

17. The method of claim 16 wherein the strap attachment further comprises a flexible tab with a space disposed in between the holder bar and the flexible tab, the method further comprising turning off the supply of pressurized gas when use of the nasal mask is completed, and disconnecting the second end of the strap from the nasal mask by rotating the strap attachment around the holder until the flexible tab snaps off of the holder.

* * * * *